US009218456B2

(12) United States Patent
Strickland et al.

(10) Patent No.: US 9,218,456 B2
(45) Date of Patent: Dec. 22, 2015

(54) COMMUNICATION PROTOCOL FOR MEDICAL DEVICES THAT SUPPORTS ENHANCED SECURITY

(75) Inventors: Raymond Strickland, Indianapolis, IN (US); Ulrich Porsch, Weinheim (DE); Daniel Birtwhistle, Fishers, IN (US)

(73) Assignee: Roche Diabetes Care, Inc., Indianapolis, IN (US)

(*) Notice: Subject to any disclaimer, the term of this patent is extended or adjusted under 35 U.S.C. 154(b) by 1315 days.

(21) Appl. No.: 12/976,224

(22) Filed: Dec. 22, 2010

(65) Prior Publication Data
US 2012/0165614 A1  Jun. 28, 2012

(51) Int. Cl.
*H04L 29/06* (2006.01)
*G06F 19/00* (2011.01)

(52) U.S. Cl.
CPC ............ *G06F 19/3412* (2013.01); *H04L 63/08* (2013.01)

(58) Field of Classification Search
None
See application file for complete search history.

(56) References Cited

U.S. PATENT DOCUMENTS

2003/0036683 A1* 2/2003 Kehr et al. .................... 600/300

OTHER PUBLICATIONS

Part 20601: Application Profile—Optimized Exchange Protocol, IEEE Std 11073-20601 Sep. 26, 2008.
Part 10417: Device Specialization—Glucose Meter, IEEE Std 11073-10417, May 8, 2009.
Continua Design Guidelines 2010, Oct. 1, 2010.
Y. Zhu et al "A Lightweight Policy System for Body Sensor Networks", IEEE Transactions on Network & Service Management, vol. 6, No. 3 (2009).
D. Halperin et al "Security and Privacy for Implantable Medical Devices", IEEE Pervasive Computing, vol. 7, No. 1 (2008).
P. Kulkarni et al "Mphasis: Mobile Patient Healthcare and Sensor Information System", Journal of Network & Computer Applications, vol. 34, No. 1 (2010).
S. Mougiakakou et al "SMARTDIAB: A Communication and Information Technology Approach for the Intelligent Monitoring, Management and Follow-up of Type 1 Diabetes Patients", IEEE Transactions on Information Technology in Biomedicine vol. 14, No. 3 (2010).
ISO/IEEE, "Health Informatics—Personal Health Device Communication", IEEE Standard (2010).
International Telecommunication Union "Information Technology—Open Systems Interconnection—Security Frameworks for Open Systems: Access Control Framework", ITU-T Standard, International Telecommunication Union No. X. 812 (1995).
International Telecommunication Union "Information Technology—Open Systems Interconnection—Security Frameworks for Open Systems: Authentication Framework", ITU-T Standard, International Telecommunication Union No. X. 811 (1995).
Skevofilakas, et al., "A Communication and Information Technology Infrastructure for Real Time Monitoring and Management of Type 1 Diabetes Patients", IEEE, Aug. 2007.
Mougiakakou et al., "A Communication Platform for Tele-Monitoring and Tele-Management of Type 1 Diabetes", IEEE, Sep. 2007.

* cited by examiner

*Primary Examiner* — Minh Dinh
(74) *Attorney, Agent, or Firm* — Harness, Dickey

(57) ABSTRACT

A diabetes management system is provided that employs a communication protocol with enhanced security. The diabetes management system includes: a medical device operable to perform a diabetes care function in relation to a patient and store data related to the operation thereof; and a diabetes care manager in data communication with the medical device using a communication protocol defined in accordance with IEEE standard 11073. The diabetes care manager is able to request access to a given security role supported by the medical device, where the given security role is associated with a set of commands that are defined as a private extension of the communication protocol.

17 Claims, 6 Drawing Sheets

COMMUNICATION PROTOCOL FOR MEDICAL DEVICES THAT SUPPORTS ENHANCED SECURITY

FIELD

The present disclosure relates to a communication protocol for medical devices used for diabetes care and, more particularly, to a communication protocol that supports enhanced security.

BACKGROUND

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and may be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. Its incidence is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Management of diabetes is complex as the level of blood glucose entering the bloodstream is dynamic. Variation of insulin in the bloodstream that controls the transport of glucose out of the bloodstream also complicates diabetes management. Blood glucose levels are sensitive to diet and exercise, but also can be affected by sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

Management of diabetes is often highly intrusive because of the need to consistently obtain reliable diagnostic information, follow prescribed therapy, and manage lifestyle on a daily basis. Daily diagnostic information, such as blood glucose concentration, is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data that are acquired from medical devices, personal healthcare devices, patient recorded information, healthcare professional tests results, prescribed medications and recorded information. Clinicians generally treat diabetic patients according to published therapeutic guidelines such as, for example, Joslin Diabetes Center & Joslin Clinic, *Clinical Guideline for Pharmacological Management of Type 2 Diabetes* (2007) and Joslin Diabetes Center & Joslin Clinic, *Clinical Guideline for Adults with Diabetes* (2008). The guidelines may specify a desired biomarker value, e.g., a fasting blood glucose value of less than 100 mg/dl, or the clinician can specify a desired biomarker value based on the clinician's training and experience in treating patients with diabetes. However, such guidelines do not specify biomarker collection procedures for parameter adjustments to support specific therapies used in optimizing a diabetic patient's therapy. Subsequently, diabetic patients often must measure their glucose levels with little structure for collection and with little regard to lifestyle factors. Such unstructured collection of glucose levels can result in some biomarker measurements lacking interpretative context, thereby reducing the value of such measurements to clinicians and other health care providers. Thus, there is a need to provide structured collection procedures for diagnostic or therapy support of a patient with diabetes or other chronic diseases.

Patients with diabetes and their healthcare professionals interact with a variety of medical devices and systems to help manage the disease. For each of these differing types of medical devices, there is a need to aggregate, manipulate, manage, present, and communicate diagnostic data and prescriptive data from multiple data sources in an efficient manner to improve the care and health of a person with diabetes, so the person with diabetes can lead a full life and reduce the risk of complications from diabetes. There is also a need to aggregate, manipulate, manage, present, and communicate such diagnostic data and prescriptive data amongst the different types of medical devices using a standard communication protocol. IEEE 11073 is an exemplary communication standard that addresses interoperability and communication amongst medical devices such as blood pressure monitors, insulin pumps and the like. Within the context of such communication protocol, there is a further need to support enhanced security. For example, different types of users require access to different types of functions and/or data supported by the system. Therefore, it is desirable to provide a system with varying security roles having varying privileges but in compliance with such communication protocols.

The background description provided herein is for the purpose of generally presenting the context of the disclosure.

SUMMARY

A diabetes management system is provided that employs a communication protocol with enhanced security. The diabetes management system includes: a medical device operable to perform a diabetes care function in relation to a patient and store data related to the operation thereof; and a diabetes care manager in data communication with the medical device using a communication protocol defined in accordance with IEEE standard 11073. The diabetes care manager is able to request access to a given security role supported by the medical device, where the given security role is associated with a set of commands that are defined as a private extension of the communication protocol.

In another aspect of the system, security roles are administered at an application level. For example, a first application is able to request access to a first security role supported by the medical device, such that the first security role is associated with a first set of commands for accessing data on the medical device; and a second application is able to request access to a second security role supported by the medical device, such that the second security role is associated with a second set of commands for accessing data on the medical device. The second set of commands having one or more commands that are mutually exclusive from the first set of commands.

Further areas of applicability of the present disclosure will become apparent from the detailed description provided hereinafter. It should be understood that the detailed description and specific examples are intended for purposes of illustration only and are not intended to limit the scope of the disclosure.

DETAILED DESCRIPTION

Figure 1:
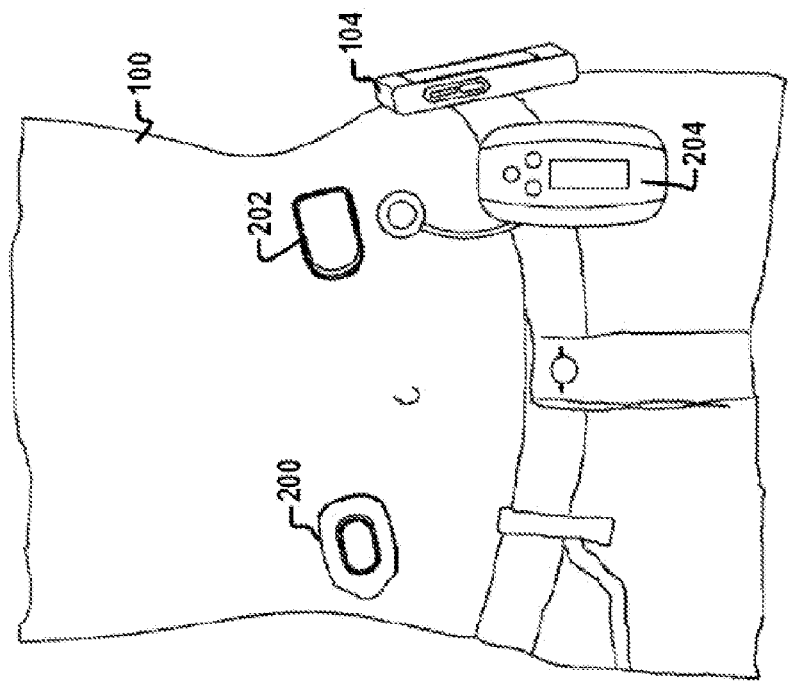
FIG. 1 is a diagram showing a patient and a treating clinician.

Referring to FIG. 1, a person 100 with diabetes and a healthcare professional 102 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician 102 a variety of patient data including blood glucose measurements, continuous glucose monitor data, amounts of insulin infused, amounts of food and beverages consumed, exercise schedules, and other lifestyle information. The clinician 102 may obtain additional patient data that includes measurements of HbAlC, cholesterol levels, triglycerides, blood pressure, and weight of the patient 100. The patient data can be recorded manually or electronically on a handheld diabetes management device 104, a diabetes analysis software executed on a personal computer (PC) 106, and/or a web-based diabetes analysis site (not shown). The clinician 102 can analyze the patient data manually or electronically using the diabetes analysis software and/or the web-based diabetes analysis site. After analyzing the patient data and reviewing adherence of the patient 100 to previously prescribed therapy, the clinician 102 can decide whether to modify the therapy for the patient 100.

Figure 2:
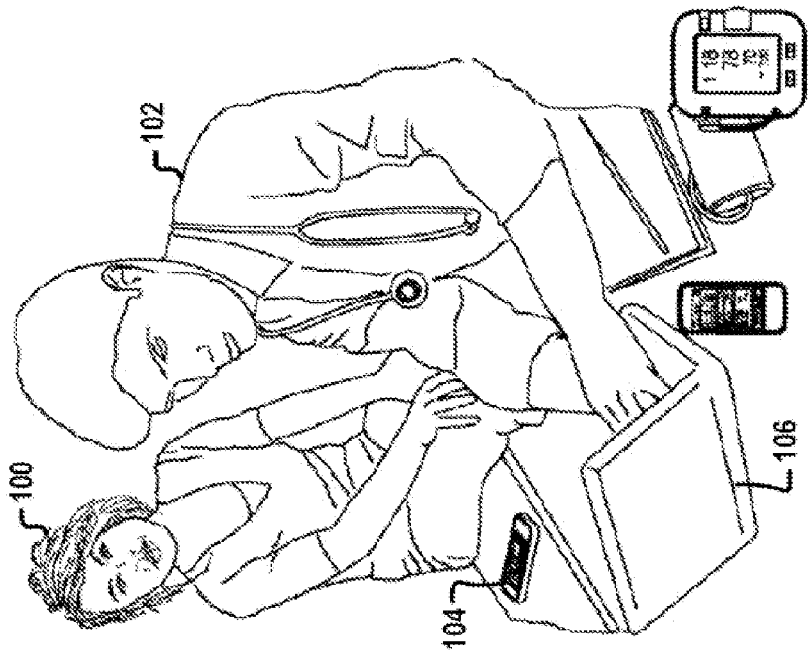
FIG. 2 is a diagram showing the patient with a continuous glucose monitor (CGM), an ambulatory durable insulin infusion pump, an ambulatory non-durable insulin infusion pump, and a diabetes manger.

Referring to FIG. 2, the patient 100 can use a continuous glucose monitor (CGM) 200, an ambulatory non-durable insulin infusion pump 202 or an ambulatory durable insulin infusion pump 204 (hereinafter insulin pump 202 or 204), and the handheld diabetes management device 104 (hereinafter the diabetes manager 104). The CGM 200 uses a subcutaneous sensor to sense and monitor the amount of glucose in the blood of the patient 100 and communicates corresponding readings to the diabetes manager 104.

The diabetes manager 104 performs various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives readings from the CGM 200 indicating insulin level in the blood of the patient 100. The diabetes manager 104 transmits instructions to the insulin pump 202 or 204, which delivers insulin to the patient 100. Insulin can be delivered in a scheduled manner in the form of a basal dose, which maintains a predetermined insulin level in the blood of the patient 100. Additionally, insulin can be delivered in the form of a bolus dose, which raises the amount of insulin in the blood of the patient 100 by a predetermined amount. While this disclosure makes reference to diabetes care, it is readily understood that the concepts disclosed herein can be applied to other types of chronic diseases and/or other types of medical devices.

Figure 3:
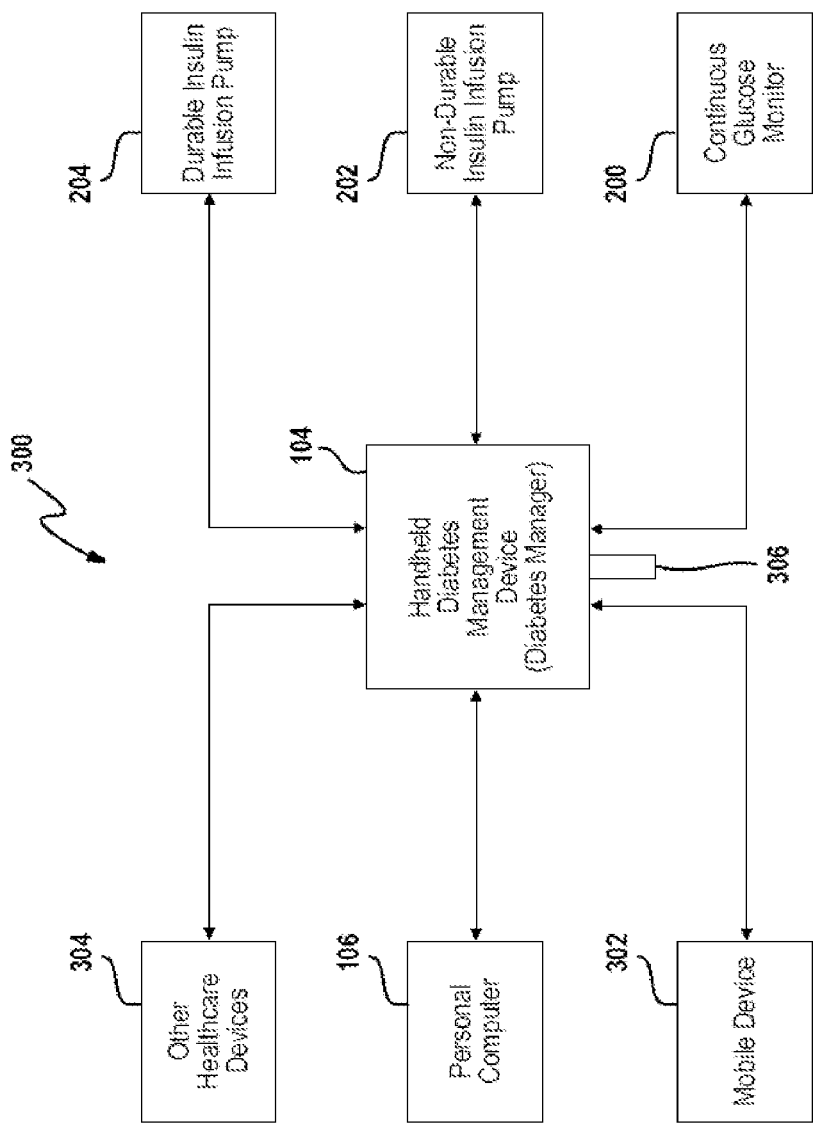
FIG. 3 is a block diagram showing an exemplary diabetes management system used by patients and clinicians to manage diabetes.

Referring to FIG. 3, a diabetes management system 300 used by the patient 100 and the clinician 102 includes one or more of the following devices: the diabetes manager 104, the continuous glucose monitor (CGM) 200, the insulin pump 202 or 204, a mobile device 302, the PC 106 with the diabetes analysis software, and other healthcare devices 304. The diabetes manager 104 is configured as a system hub and communicates with the devices of the diabetes management system 300. Alternatively, the insulin pump 204 or the mobile device 302 can serve as the system hub. Communication between the devices in the diabetes management system 300 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 100 and clinician 102 to exchange information.

The diabetes manager 104 can receive blood glucose readings from one or more sources (e.g., from the CGM 200). The CGM 200 continuously measures the blood glucose level of the patient 100. The CGM 200 periodically communicates the blood glucose level to the diabetes manager 104. The diabetes manager 104 and the CGM 200 communicate wirelessly using a proprietary wireless protocol (e.g., Gazell wireless protocol developed by Nordic Semiconductor, Inc.)

Additionally, the diabetes manager 104 includes a blood glucose meter (BGM) and a port that communicates with the BGM (not shown). The port can receive a blood glucose measurement strip 306. The patient 100 deposits a sample of blood or other bodily fluid on the blood glucose measurement strip 306. The BGM analyzes the sample and measures the blood glucose level in the sample. The blood glucose level measured from the sample and/or the blood glucose level read by the CGM 200 can be used to determine the amount of insulin to be administered to the patient 100. To facilitate collection of blood glucose measures, the diabetes manager 104 may executes one or more structured collection procedures as further described below.

The diabetes manager 104 communicates with the insulin pump 202 or 204. The insulin pump 202 or 204 can be configured to receive instructions from the diabetes manager 104 to deliver a predetermined amount of insulin to the patient 100. Additionally, the diabetes manager 104 can receive other information from the patient including meal and/or exercise schedules of the patient 100. The diabetes manager 104 can determine the amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wireline communication protocols can also be used.

In addition, the diabetes manager 104 can communicate with the other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 may use communication protocols compliant with ISO/IEEE 11073. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other interfaces. A diabetes management software running on the PC 106 includes an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth. The mobile device 302 may include a cellular phone, a pager, or a personal digital assistant (PDA). The diabetes manager 104 can send data to an external network through the mobile device 302. The mobile device 302 can transmit messages to the external network upon receiving data from the diabetes manager 104.

Figure 4:
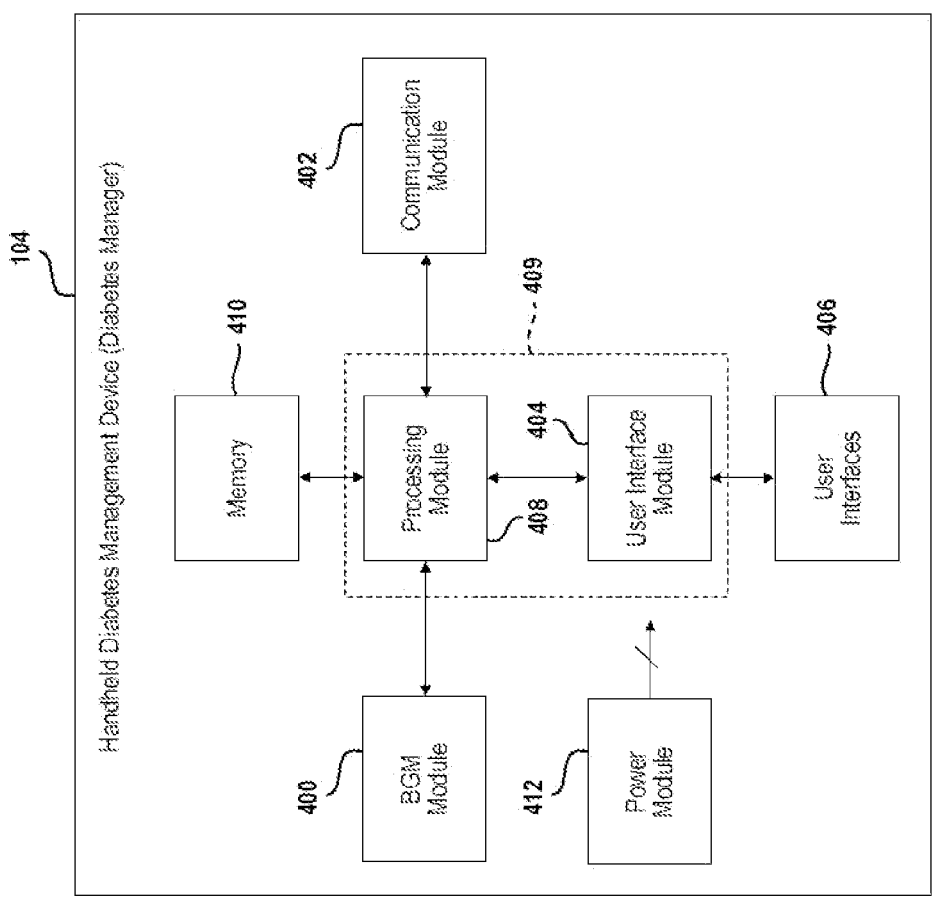
FIG. 4 is a functional block diagram of a diabetes manager.

An exemplary diabetes manager 104 is further described in relation to FIG. 4. The diabetes manager 104 comprises a blood glucose measuring (BGM) module 400, a communication module 402, a user interface module 404, user interfaces 406, a processing module 408, memory 410, and a power module 412. The user interface module 404 and the processing module 408 can be implemented by an application processing module 409. The BGM module 400 includes a blood glucose measuring engine that analyzes samples provided by the patient 100 on the blood glucose measurement strip 306 and that measures the amount of blood glucose in the samples. The communication module 402 includes multiple radios that communicate with different devices of the diabetes management system 300. The user interface module 404 interfaces the diabetes manager 104 to various user interfaces 406 that the patient 100 can use to interact with the diabetes manager 104. For example, the user interfaces 406 can include keys, switches, a display, a speaker, a microphone, a secure digital (SD) card port, a USB port, etc. (not shown).

The processing module 408 processes data received from the BGM module 400, the communication module 402, and the user interface module 404. The processing module 408 uses memory 410 for processing and storing data. The memory 410 can include volatile and nonvolatile memory. The processing module 408 outputs data to and receives data from the user interfaces 406 via the user interface module 404. The processing module 408 outputs data to and receives data from the devices of the diabetes management system 300 via the communication module 402. The power module 412 supplies power to the components of the diabetes manager 104. The power module 412 may include a rechargeable battery. The battery can be recharged using an adapter that plugs into a wall outlet. The battery can also be charged via the USB port of the diabetes manager 104.

ISO/IEEE 11073 standard enables communication amongst medical devices and other computer systems. By way of background, ISO/IEEE 11073 standard is based on an object oriented systems management paradigm. The overall system model is divided into three principal components: the domain information model (DIM), the service model, and the communication model. These three components work together to represent data, define data access and command methodologies and communicate the data from an agent to a manager. ISO/IEEE 11073-20601 may be referenced for a detailed description of the modeling constructs although each is described briefly below.

Figure 5:
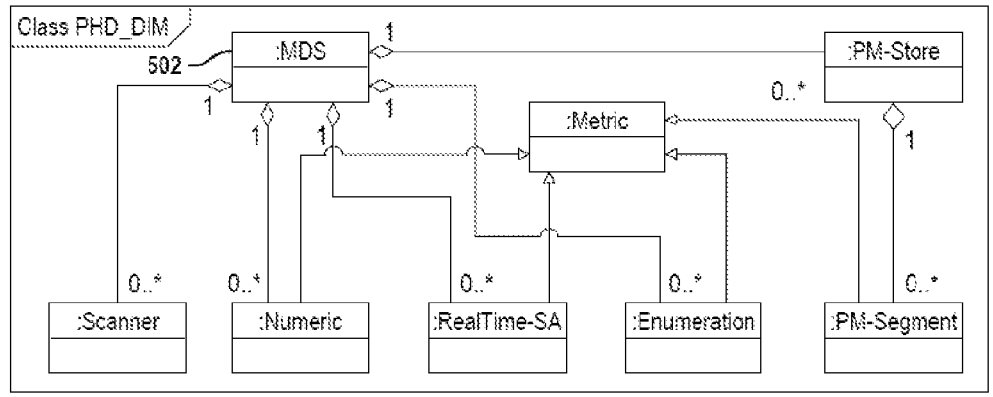
FIG. 5 is a class diagram for a personal health device defined in accordance with ISO/IEEE 11073-20601.

The domain information model is a hierarchical model that describes an agent as a set of objects. These objects and their attributes represent the elements that control behavior and report on the status of the agent and the data that an agent can communicate to a manager. With reference to FIG. 5, a class diagram for a personal health device is defined in accordance with ISO/IEEE 11073-20601. The Medical Device System class 502 is the root class of the device and contains attributes defining the device itself. Exemplary attributes include the type of device, e.g., glucose meter or insulin pump, manufacturer and model information and registered certification information. All other object classes are derived from the MDS class. For example, the Numeric class represents numeric measurements such as bG, carbohydrates, bolus amount, etc; whereas, the enumeration class represents status information and/or annotation information. For brevity purposes, a description is not provided for all of the classes shown in the figure.

Communication between the agent and the manager is defined by the application protocol in ISO/IEEE 11073-20601. The service model defines the conceptual mechanisms for the data exchange services. Object access services, such as Get, Set, Action and Event Reports, are mapped to messages that are exchanged between the agent and the manager. Protocol messages within the ISO/IEEE 11072 series of standards are defined in Abstract Syntax Notation One (ASN. 1).

The messages defined in ISO/IEEE 11073-20601 can coexist with messages defined in other standard application profiles defined in the ISO/IEEE 11072 series of standards.

In general, the communication model supports the topology of one or more agents communicating over logical point-to-point connections to a single manager. More specifically, the communication model defines the construct of an application protocol data unit (APDU). ADPUs are data packets exchanged between agents and managers. For each logical point-to-point connection, the dynamic system behavior is defined by a connection state machine as specified in ISO/IEEE 11073-20601.

Two types of configuration are defined in ISO/IEEE 11073-20601: standard and extended. Standard configurations are defined in the ISO/IEEE 11073-104zz specializations (such as the ISO/IEEE 11073-10417 Glucose Device specialization) and are assigned a well-known identifier (Dev-Configuration-Id). In extended configurations, the agent's configuration is not predefined in the standard. The agent determines which objects, attributes, and values will be used in a configuration and assigns a configuration identifier. The usage of a standard or extended configuration is negotiated at association time between the agent and the manager.

Figure 6:
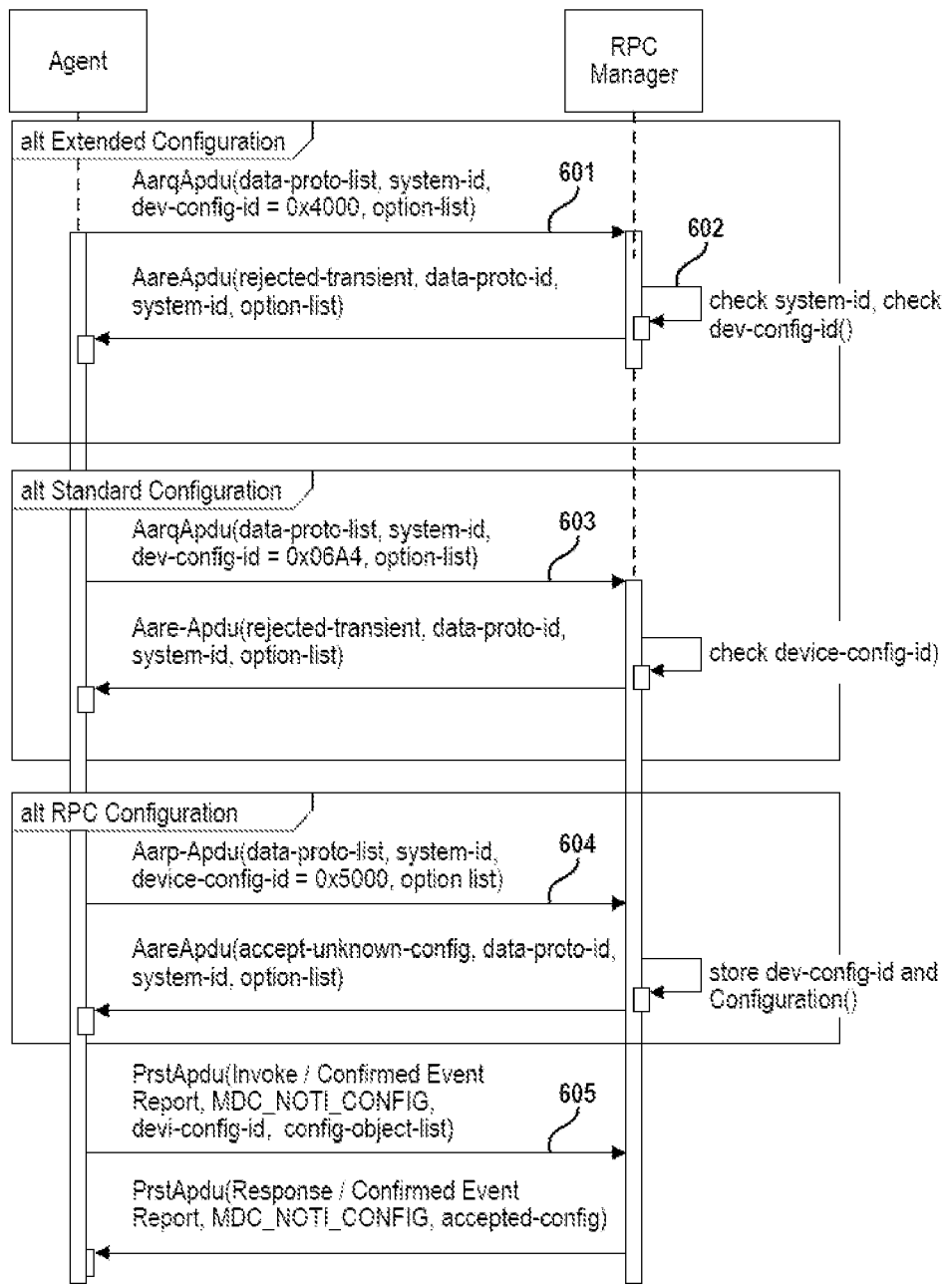
FIG. 6 is a sequence diagram illustrating a negotiation process between an agent and a manager.

FIG. 6 is a sequence diagram illustrating a negotiation process implemented in accordance with this disclosure. The agent first sends an association request 601 that specifies the extended configuration to the manager. Upon receipt of the request, the manager checks at 602 the system identifier and the configuration identifier. A reply is then sent from the manager to the agent. If the manager accepts the request from the agent, then the agent can begin sending measurements immediately to the manager. If the manager denies the request, then the agent sends a second association request 602 that specifies the standard configuration. Upon receipt of the second request, the manager again checks the request and sends a reply to the agent. If both devices are defined in compliance with ISO/IEEE 11073-20601, the devices will communicate using the standard configuration.

The agent and manager may be configured to support a third configuration. To support the third configuration, the manager is configured to deny both association requests. The agent is also configured to send a third association request 603 that identifies the third configuration. In the third configuration, the agent and manager will have access (amongst other objects and attributes) to security authorization commands which will be further described below.

Typically, the manager does not recognize the agent's configuration on the first connection, so the manager responds that the agent needs to send the configuration information as a configuration event report. In this case, the agent will send the configuration event report at 605 to the manager. If, however, the manager already understands the configuration, either because it was preloaded in some way or the agent had previously associated with the manager, then the manager responds that the configuration is known and no further configuration information needs to be sent.

Figure 7:
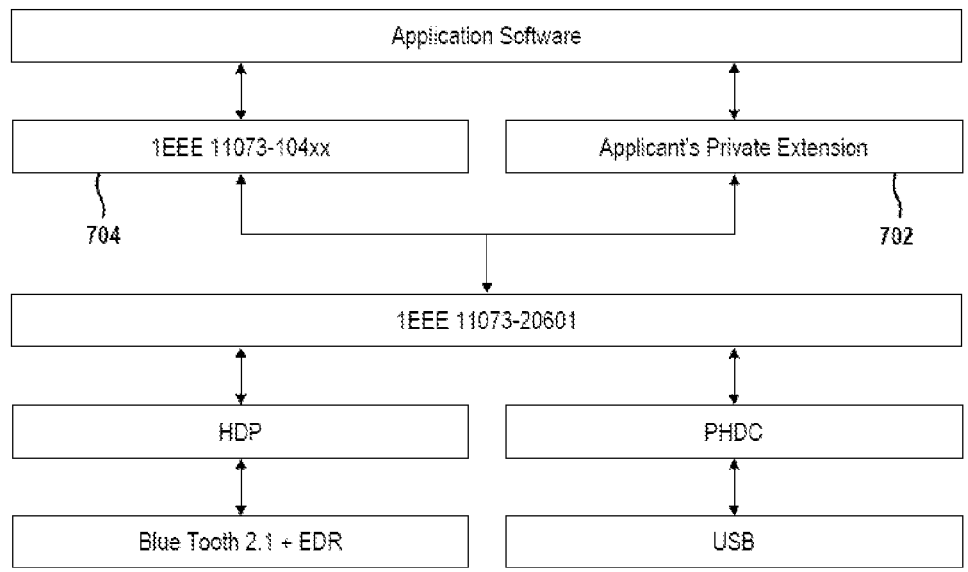
FIG. 7 is a block diagram depicting how applicant's private extension relates to the standardized communication protocols.

With reference to FIG. 7, this disclosure defines an extension 702 to these configurations, i.e., applicant's private extension, which is not published in any of the ISO/IEEE 11073-104xx device specializations 704. The relationship of applicant's private extension 702 to the standardized communication protocols is shown in FIG. 7. Generally speaking, implementation of this private extension 702 defines the attributes and services to support the transfer and execution of specific commands and data. A basic framework for the private extension is first described below. Within this framework, a set of action commands that support enhanced security are then presented by this disclosure.

In an exemplary embodiment of applicant's private extension, each agent device has one MDS object. This top-level MDS object is instantiated from the MDS class. The MDS object represents the identification and status of the agent through its attributes. Beyond the class definition provided by the IEEE standards, additional standardized classes may be supported by the agents and managers in accordance with applicant's private extension. The additional standardized classes are referred to herein as RPC classes. RPC private nomenclature codes are assigned from the manufacturer-specific range of private term codes (0xF000-0xFBFF) within the object oriented partition category (MDC_PART-OBJ). The partition number for object oriented classes and objects is one.

The attributes for each RPC class are defined in tables that specify the name of the attribute, its value and its qualifier. The qualifiers mean M—attribute is mandatory, C—attribute is conditional and depends on the condition stated in the remark or value column, R—attribute is recommended, NR—attribute is not recommended, and O—attribute is optional. Mandatory attributes shall be implemented by an agent. Conditional attributes shall be implemented if the condition applies and may be implemented otherwise. Recommended attributes should be implemented by the agent. Not recommend attributes should not be implemented by the agent. Optional attributes may be implemented on an agent.

RPC classes that instantiate numeric type objects are created as they exist in the device. These numeric type objects represent additional result data that can be obtained from the device in the same manner they are obtained from the device specialization. These objects shall be added to the device attribute value map for authenticated managers. Attributes common across all of the RPC numeric objects are set forth in Appendix A. Furthermore, applicant's private extension has defined a few RPC numeric objects available to system designers Likewise, definitions for these common RPC numeric objects are set forth in Appendix A. Applicant's private extension also defines a few RPC enumeration objects as set forth in Appendix B.

Applicant's private extension further defines an application protocol data unit as set forth below. An APDU represents the top-level message frame of the personal health device protocol. The extended APDU is added as an extension to the standard list of APDUs defined in the ISO/IEEE 11073-20601 specification.

```
Apdu Type ::=CHOICE {
aarg [57856]   AarqApdu, -- Association Request [0xE200]
aare [58112]   AareApdu, -- Association Response [0xE300]
rlrq [58368]   RlrqApdu, -- Association Release Request [0xE400]
rlre [58624]   RlreApdu, -- Association Release Response [0xE500]
abrt [58880]   AbrtApdu, -- Association Abort [0xE600]
prst [59136]   PrstApdu, -- Presentation APDU [0xE700]
prrp [61440]   PrrpApdu - applicant's extended APDU [0xF000] }
```

A presentation APDU as defined in ISO/IEEE 11073-20601 is simply an octet string. Applicant's extended APDU adds a 16-bit CRC in order to ensure data integrity beyond the level provided by the transport and the ISO/IEEE 11073-20601 concept of reliable data channels. With this CRC, corrupted data can be detected by the application. This CRC covers the entire "RPC" part of the command invoke and command response APDUs.

```
PrrpApdup ::= SEQUENCE {
    data    OCTET STRING, (ENCODED VERSION OF DataApdu)
    crc     INT-U16 (checksum over the entire data field) }
```

Applicant's extended APDU shall encapsulate unconfirmed Action Argument and confirmed Event Report Data APDUs defined by the ISO/IEEE 11073-20601 standard as follows:

```
ActionArgumentSimple ::= SEQUENCE {
    obj-handle    HANDLE
    action-type   OID-Type,    --From the nom-part-obj partition
                               --Subpartition ACT (MDC_ACT_*)
    Action-info-args ANY DEFINED BY action-type }
```

```
EventReportArgumentSimple ::=SEQUENCE {
    obj-handle  HANDLE
    event-time  Relative Time,
    event-type  OID-Type    --From the nom-part-obj partition
                            --Subpartition NOTI (MDC_NOTI_*)
    event-info  ANY DEFINED BY event-type
```

The approach used to invoke applicant defined commands is to extend the MDS object methods with applicant defined actions. The ISO/IEEE 11073-20601 unconfirmed action service uses the ActionArgumentSimple structure described above.

For the purposes of this specification, the fields would have the following values:

| | |
|---|---|
| handle | 0 (for the MDS object) |
| action-type | manufacturer specific code for applicant defined actions |
| action-info-args | manufacturer specific structure for each applicant defined action |

In order to invoke an applicant defined command, a manager would populate the action-type and action-info-arts of the ActionArgumentSimple object as follows:

| | |
|---|---|
| action-type | MDC_ACT_RPC_COMMAND_INVOKE |
| action-info-args | RpcCommandArguments |

The data objects used for command invocation action-info-args are defined as follows:

```
RpcCommandArguments ::= SEQUENCE {
    cmd-subcmd  INT-U16;   //Command/subcommand combined
    arguments   RpcDataArguments [ ]; }
```

```
RpcDataArguments ::= SEQUENCE {
    type    INT-U16;
    data    ANY DEFINED BY type }
```

The encoding of ANY DEFINED BY is defined in ISO/IEEE 11073-20601 as follows. The ANY DEFINED BY type (ASN. 1 1988/90) or the instance-of type (ASN. 1 1994) is encoded by a header of a length field to specify the number of octets in the encoding of the selected value that follows. The length element shall be expressed as the number of bytes (octets) contained in the value element. An empty argument shall be indicated with the type element set to RPC_ARG_TYPE_EMPTY, the length element set to 2 and the value element set to zero as an INT-U16. An RpcCommandArguments structure which contains a cmd-subcmd value that requires no arguments will include a single RpcDataArguments element indicating an empty argument.

The approach used to return data as a result of an applicant defined command invocation is to extend the MDS event reports with applicant defined events. The ISO/IEEE 11073-20601 confirmed notification service uses the EventReportArgumentSimple structure previously discussed in this disclosure. For the purposes of this disclosure, the fields would have the following values:

| | |
|---|---|
| Handle | 0 (for the MDS object) |
| event-time | 0 (event time is not used for applicant actions) |
| event-type | manufacturer specific code for applicant defined command responses. - |
| event-info | manufacturer specific structure for each applicant defined response. |

In order to respond to an applicant defined command, an agent would populate the event-type and event-info of the EventReportArgumentSimple object as follows:

| | |
|---|---|
| Event-type | MDC_NOTI_RPC_COMMAND_RESPONSE |
| event-info | RpcDataArguments [ ] |

The RpcDataArguments object is the same as is defined for applicant defined actions.

Methods (actions) available for the MDS object are defined in the table below. These methods are invoked using the ACTION service. In the table, the Method/Action column defines the name of the method. The Mode column defines whether the method is invoked as an unconfirmed action (i.e., roiv-cmip-action) or a confirmed action (i.e., roiv-cmip-confirmed-action). The Action-type column defines the nomenclature ID to use in the action-type field of an action request and response. The action-info-args column defines the associated data structure to use in the action message for the action-info-args field of the request. The resulting action-info-args column define the structure to use in the action-info-args of the response.

| Method/Action | Mode | Action-type | Action-info-args | Resulting action-info-args |
|---|---|---|---|---|
| RFC-Command-Invoke | Unconfirmed | MDC_ACT_RPC_COMMAND_INVOKE | RpcCommandArguments | n/a |

This method allows the manager to invoke an applicant defined system command.

Potential events sent by the RPC object are defined in the table below. A manager shall support all methods defined in the table.

| Method/Action | Mode | Event-type | Event-info Parameter | Event-reply-info |
| --- | --- | --- | --- | --- |
| RPC-Data-Event | Confirmed | MDC_NOTI_RPC_COMMAND_RESPONSE | RpcDataArguments | RpcDataArguments |
| RPC-Error-Event | Confirmed | MDC_NOTI_RPC_ERROR_RESPONSE | RpcDataArguments | RpcDataArguments |

For the command response event, after the execution of an applicant defined command has been requested via the ACTION service, the agent will process the command, sub-command and parameter objects. If there are no command parameter errors, the result will be an agent-initiated event report reflecting the result of successful command processing. In the case of command success, the event report will contain a command-specific result string of data as defined by this specification.

For the error response event, after the execution of an applicant defined command has been requested via the ACTION service, the agent will process the command, sub-command and parameter objects. If there are parameter errors, the result will be an agent-initiated event report specifying the parameter error. If a manager receives an RPC_ERR_HARDWARE or RPC_ERR_APPLICATION response, the manager should invoke the RPC Read and Clear Status command to retrieve further error information available from the device.

In order to partition various types of users and their access to different functions, a security role concept has been established within this framework. This principle defines that each manager or its applications must be able to access only the information and resources that are necessary for its legitimate purposes. For illustrative purposes, a diabetes care manager may be a personal computer or an application residing thereon that is seeking access to an agent, such as another type of medical device. It is understood that the diabetes care manager may be other types of devices, such as the handheld diabetes management device 104. Likewise, different types of medical devices may act as agents including but not limited to continuous glucose monitors or insulin infusion pumps.

Security roles are divided into three general categories of access: public access, licensed vendor access and proprietary access. Public commands and objects are used for transferring and acting on public information that is documented in an open standard, such as IEEE 11073 or Continua. These commands and objects are available to all diabetes care managers and require no authentication. Licensed vendor commands and objects are used for transferring and acting on device information, but they do not impact safety-related device parameters. These commands and objects are available to a subset of user roles. In order to use these commands and objects, the diabetes care manager must complete a minimal level of authentication with the agent. Proprietary commands may impact safety-related device parameters and thus require a higher level of authentication between the diabetes care manager and the agent. Although a security role may be established for each category, there may also be more that one security role defined in each category. Additional categories are also contemplated.

Different types of exemplary security roles are further described below. A core role provides access to public commands and is available to any diabetes care manager. For example, the core role provides access to commands that are defined in the IEEE 11073 specialized functionality standard. In this role, no authentication measures are taken in addition to those defined in the device specialization.

A core plus role is used to provide access to third party licensed vendors. This role provides access to class numeric and enumeration objects as well as a limited number of proprietary commands. For example, commands that enable reading of parameters but not manipulation of parameters would be accessible in this role. In another example, this role may provide access to commands for manipulating user interface parameters. The agent may require a limited form of authentication, such as a static password, to gain access to this security role.

Proprietary security roles may be tailored to certain functions. For example, there may be a service role designed for trouble shooting problems experienced by a medical device. This role may support commands for accessing error logs or measurement logs but with limited write capabilities. This role is intended for use by customer service representatives.

A therapy role provides access to commands that affect a patient's therapeutic treatment, such as bolus advice setting, insulin pump configurations or parameters of a basal insulin titration structured test. This role is intended for use by health care professionals.

An upgrade role provides access to commands that are used to perform field upgrades of the device. For example, it may be desirable to upgrade firmware and/or internal database files on a meter. This role is intended to use by an information systems specialist.

A production role provides access to all objects and commands. This type of role may be used for initial configuration and setup of a device. This role is intended for use in the manufacturing environment before devices get into the field.

Each of these proprietary security roles requires some level of authentication. Even amongst the proprietary security roles, there may be some roles, such as upgrade or production roles, that require a higher level of security. While there may be some overlap amongst the objects and/or commands associated with different security roles, there are other objects and/or commands that are exclusively assigned to one of the security roles. Furthermore, while a few exemplary security roles have been set forth, it is readily understood that other types of security roles fall within the broader aspects of this disclosure.

To gain access to a given security role, the manager will send an authentication request to the agent. The authentication request includes an authentication factor as well as other appropriate authenticating information. The agent is responsible for verifying the level of access that is requested by the manager and responding with an appropriate reply.

Figure 8:
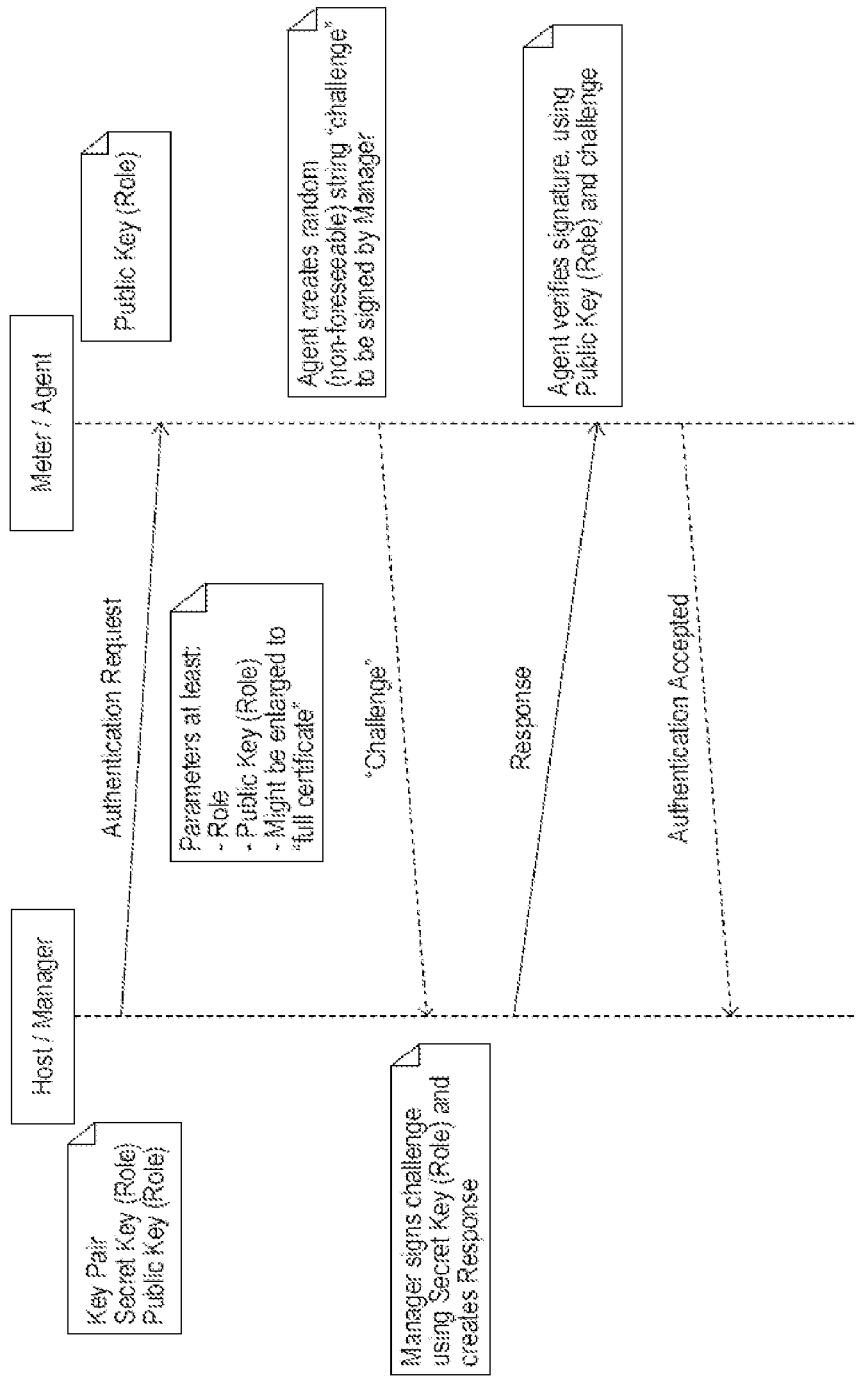
FIG. 8 is a sequence diagram illustrating an exemplary authentication procedure between a manager and an agent The drawings described herein are for illustrative purposes only of selected embodiments and not all possible implementations, and are not intended to limit the scope of the present disclosure. Corresponding reference numerals indicate corresponding parts throughout the several views of the drawings.

FIG. 8 further illustrates an exemplary authentication procedure that may be used between a manager and an agent. In this exemplary embodiment, each available security role is assigned a different public/private key pair. For example, the therapy security role is assigned a first key pair and the upgrade role is assigned a second key pair. Each key pair is issued by a certification authority to an appropriate manager device or more particularly to an application residing on a manager device.

The manager sends a request to access a particular security role to the agent. In a simplified embodiment, the request identifies the requested role and includes the corresponding public key for that role. In a more robust embodiment, the manager sends a digital certificate created with the corresponding key pair. In either case, the agent formulates a challenge for the manager. In one embodiment, the challenge is a random string that is to be signed by the manager. Other types of challenges could be employed as well. The challenge is then sent by the agent to the manager.

Upon receipt of the challenge, the manager signs the challenge using the corresponding private key and sends the signed challenge back to the agent. The agent verifies the signature to complete the authentication procedure. If verified, the manager has access to objects and commands associated with the requested security role. If the signature does not pass verification, the agent sends an appropriate error message to the manager. Other types of authentication procedures are also within the scope of this disclosure.

In an exemplary embodiment, the authentication procedure is implemented using a set of authentication commands that are defined in applicant's private extension of IEEE standard 11073. More specifically, the command for performing security authorization is RPC_CMD_SECURITY and has a value of 0x8300. This command must be "OR-ed" with one of the security subcommand values to form a complete command-subcommand value. In the exemplary embodiment, security subcommands include an authentication request command and an authentication signed challenge command. Each of these commands are set forth in detail below.

The authentication request command is sent by the manager to request a particular authorization role. The manager specifies the role requested and presents a corresponding role public key. The command response returned by the agent constitutes an authentication challenge, and contains a challenge string. An exemplary command definition is as follows:

Command/Subcommand=0x8301

Input parameters:

| Role | Number |
|---|---|
| Role Key | UINT 8 array |

Output parameters:

| Command Error Response (if parameters are not valid) | |
|---|---|
| Error Code | Number |
| Challenge Response (if there are no errors to report) | |
| Challenge | UINT 8 array. |

RPC Command Invocation:

| cmd-subcmd | RPC_CMD_SECURITY \| RPC_SUBCMD_AUTHENTICATION_REQUEST |
|---|---|
| RpcDataArguments[0].type | RPC_ARG_TYPE_UINT16 |
| RpcDataArguments[0].length | 2 |
| RpcDataArguments[0].value | Role enumeration value |
| RpcDataArguments[1].type | RPC_ARG_TYPE_UINT8_ARRAY |
| RpcDataArguments[1].length | Length of Role Key data array |
| RpcDataArguments[1].value | Role Key data array value |

RPC Command Response:

| obj-handle | 0x0000 |
|---|---|
| event-time | 0xFFFFFFFF |
| event-type | MDC_NOTI_RPC_COMMAND_RESPONSE |
| RpcDataArguments[0].type | RPC_ARG_TYPE_UINT8_ARRAY |
| RpcDataArguments[0].length | Length of Challenge Response data array |
| RpcDataArguments[0].value | Challenge Response data array value |

RPC Command Error Response:

| obj-handle | 0x0000 |
|---|---|
| event-time | 0xFFFFFFFF |
| event-type | MDC_NOTI_RPC_ERROR_RESPONSE |
| RpcDataArguments[0].type | RPC_ARG_TYPE_UINT16 |
| RpcDataArguments[0].length | 2 |
| RpcDataArguments[0].value | Error code enumeration value |

The authentication signed challenge command is sent by the manager as the second step in the authorization process. The manager presents a signed version of the challenge response string returned by the agent's authentication request command response. The agent returns an error code indicating success (RPC_ERR_NO_ERRORS) or failure (RPC_ERR_SECURITY_ERROR). An exemplary command definition is as follows:

Command/Subcommand=0x8302
Input parameters:

| Signed Challenge | UINT 8 array |
|---|---|

Output parameters:

| Error Code | Number |
|---|---|

RPC Command Invocation:

| cmd-subcmd | RPC_CMD_SECURITY \| RPC_SUBCMD_SIGNED_CHALLENGE |
|---|---|
| RpcDataArguments[0].type | RPC_ARG_TYPE_UINT8_ARRAY |
| RpcDataArguments[0].length | Length of Signed Challenge data array |
| RpcDataArguments[0].value | Signed Challenge data array value |

RPC Command Response:

| obj-handle | 0x0000 |
|---|---|
| event-time | 0xFFFFFFFF |
| event-type | MDC_NOTI_RPC_ERROR_RESPONSE |
| RpcDataArguments[0].type | RPC_ARG_TYPE_UINT16 |
| RpcDataArguments[0].length | 2 |
| RpcDataArguments[0].value | Error code enumeration value |

Security roles may also be administered at an application level. In this arrangement, two or more different applications may reside on the manager. A first application residing on the manager may request access to a first security role supported by the medical device; whereas, a second application residing on the diabetes care manager may request access to a second security role supported by the medical device. The first security role is associated with a first set of commands for accessing data on the medical device and the second security role is associated with a second set of commands for accessing data on the medical device, such that second set of commands having one or more commands that are mutually exclusive from the first set of commands. For example, the first application upgrades the software on the medical device using the first set of commands and the second application accesses and manipulates parameters of a structured collection procedure using the second set of commands. In this way, different applications can be granted different privileges in support of different functions.

In view of the foregoing disclosure, a diabetes management system has been disclosed that employs a communication protocol with enhanced security. The diabetes management system include: a medical device that performs a diabetes care function in relation to a patient and store data related to the operation thereof; and a diabetes care manager in data communication with the medical device using a communication protocol defined in accordance with IEEE standard 11073 and is operable to request access to a given security role supported by the medical device, wherein the given security role is associated with a set of commands that are defined as a private extension of the communication protocol. The medical device may support a plurality of security roles, including a first security role associated with a first set of commands for accessing data and a second security role associated with a second set of commands for accessing data, such that the second set of commands having one or more commands that are mutually exclusive from the first set of commands.

In some aspects of the disclosure, the diabetes care manager authenticates with the medical device using a set of authentication commands, where the set of authentication commands are defined as a private extension of the communication protocol. The diabetes care manager authenticates with the medical device using a public key assigned to the given security role. The diabetes care manager further issues a request command from the set of commands to the medical device, and the medical devices receives the issued request command and issues a response command in response thereto when the diabetes care manager is authenticated by the medical device.

In other aspects of the disclosure, the medical device is configured with software and the diabetes care manager upgrades the software on the medical device using the set of commands. The medical device also executes a structured collection procedure to obtain measures of a physiological variable from a patient and the diabetes care manager accesses and manipulates parameters of the structured collection procedure using the set of commands.

In further aspects of the disclosure, the diabetes care manager issues a request command from another set of commands to the medical device without authenticating with the medical device, and the medical device receives the issued request command and issues a response command in response thereto, such that the another set of commands are defined in the IEEE standard 11073.

In another aspect of the disclosure, a medical device system is disclosed that employs a communication protocol with enhanced security. The medical device system includes: a medical device that supports a plurality of security roles for accessing the data residing thereon; a data manager in data communication with the medical device using a communication protocol defined in accordance with IEEE standard 11073; a first application residing on the manager and operable to request access to a first security role supported by the medical device, wherein the first security role is associated with a first set of commands for accessing data on the medical device; and a second application residing on the manager and operable to request access to a second security role supported by the medical device, wherein the second security role is associated with a second set of commands for accessing data on the medical device, the second set of commands having one or more commands that are mutually exclusive from the first set of commands and the first and second set of commands are defined as a private extension of the communication protocol.

In some aspects of the disclosure, the data manager authenticates with the medical device using a set of authentication commands, where the set of authentication commands are defined as a private extension of the communication protocol. The data manager also issues a request command from the set of commands to the medical device, and the medical devices receives the issued request command and issues a response command in response thereto when the data manager is authenticated by the medical device.

In other aspects of the disclosure, the diabetes care manager authenticates with the medical device using applicable public keys, where the first application has a first public key assigned to the first security role and the second application has a second public key distinct from the first public key and assigned to the second security role.

The above description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Appendix A

Common RPC Numeric Object Attributes

| Attribute Name | Value | Qualifier |
| --- | --- | --- |
| Handle | The Handle attribute represents a reference ID for this object. Each object shall have a unique ID assigned by the agent. | M |
| Type | Defined in each of the numeric objects. | M |
| Metric-Spec-Small | mss-avail-intermittent | mss-avail-stored-data | mss-upd-aperiodic | mss-msmt-aperiodic | mssacc-agent-initiated | mss-cat-manual. | M |
| Unit-Code | Defined in each of the numeric objects. | O |
| Attribute-Value-Map | Defined in each of the numeric objects | M |
| Absolute-Time-Stamp | AbsoluteTime as defined in ISO/IEEE 11073-20601 | M |
| Basic-Nu-Observed-Value | This attribute defines the numerical observed value of the object, without any further embedded status information, but with a smaller numerical representation compared to Simple-Nu-Observed-Value. One and only one of Simple-Nu-Observed-Value, Basic-Nu-Observed-Value or Nu-Observed-Value shall be present. | C |
| Simple-Nu-Observed-Value | This attribute defines the numerical observed value of the object, without any further embedded status information as found in Nu-Observed-Value. One and only one of Simple-Nu-Observed-Value, Basic-Nu-Observed-Value, or Nu-Observed-Value shall be present. | C |
| Nu-Observed-Value | This attribute defines the numerical observed value of the object and combines it with measurement status and unit information. It is used when status/unit are dynamic and are always provided together with the value. One and only one of Simple-Nu-Observed-Value, Basic-Nu-Observed-Value or Nu-Observed-Value shall be present. | |

Pen/Syringe Insulin ID

| Attribute Name | Value | Qualifier |
| --- | --- | --- |
| Type | MDC_PART_OBJ MDC_CTXT_RPC_PENSYR_INS_ID | M |
| Attribute-Value-Map | MDC_ATTR_NU_BAL_OBS_BASIC, then MDC_ATTR_TIME_STAMP_ABS | M |
| Absolute-Time-Stamp | AbsoluteTime as defined in ISO/IEEE 11073-20601 | M |
| Basic-Nu-Observed-Value | See ISO/IEEE 11073-20601—This indicates the Insulin ID value, ranging from 1 to 255 | M |

Pen/Syringe Insulin Bolus Amount

| Attribute Name | Value | Qualifier |
| --- | --- | --- |
| Type | MDC_PART_OBJ MDC_CTXT_RPC_PENSYR_BOLUS_AMT | M |
| Unit-Code | MDC_DIM_X_INTL_UNIT | M |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601 | M |
| Basic-Nu-Observed-Value | See ISO/IEEE 11073-20601—This indicates a pen/syringe insulin dose in International Units (IU), ranging from 0.0 to 999.9 | M |

Insulin Bolus Recommendation

| Attribute Name | Value | Qualifier |
| --- | --- | --- |
| Type | MDC_PART_OBJ \| MDC_CTXT_RPC_BOLUS_RECOMMENDATION | M |
| Unit-Code | MDC_DIM_X_INTL_UNIT | M |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601. | M |
| Basic-Nu-Observed-Value | See ISO/IEEE 11073-20601—This indicates a pen/syringe insulin dose in International Units (IU), ranging from 0.0 to 999.9 | M |

Pump Insulin Bolus Amount

| Attribute Name | Value | Qualifier |
| --- | --- | --- |
| Type | MDC_PART_OBJ \| MDC_CTXT_RPC_PUMP_BOLUS_AMT | M |
| Unit-Code | MDC_DIM_X_INTL_UNIT | O |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601. | M |
| Basic-Nu-Observed-Value | See ISO/IEEE 11073-20601—This indicates a pump insulin dose in International Units (IU), ranging from 0.0 to 999.9 | M |

Pump Temporary Basal Rate

| Attribute Name | Value | Qualifier |
| --- | --- | --- |
| Type | MDC_PART_OBJ \| MDC_CTXT_RPC_PUMP_TEMP_BASAL_RATE | M |
| Unit-Code | MDC_DIM_X_INTL_UNIT_PER_HR \| MDC_DIM_PERCENT | O |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601. | M |
| Basic-Nu-Observed-Value | See ISO/IEEE 11073-20601—This indicates the insulin pump's temporary basal rate in International Units per hour (IU/hr), ranging | M |

| Attribute Name | Value | Qualifier |
|---|---|---|
| | from 0.0 to 999.9, or as a percentage ranging from 0.0 to 100.0 | |

Pump Temporary Basal Duration
Insulin Pump's Temporary Basal Duration BCD Number (hhmm) 0x0000-0x9959

| Attribute Name | Value | Qualifier |
|---|---|---|
| Type | MDC_PART_OBJ \| MDC_CTXT_RPC_PUMP_TEMP_BASAL_DURATION | M |
| Unit-Code | | O |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601. | M |
| Basic-Nu-Observed-Value | See ISO/IEEE 11073-20601—This indicates the insulin pump's temporary basal duration in hours and minutes (BDC format). | M |

Pump Wave Amount

| Attribute Name | Value | Qualifier |
|---|---|---|
| Type | MDC_PART_OBJ \| MDC_CTXT_RPC_PUMP_WAVE_AMT | M |
| Unit-Code | MDC_DIM_X_INTL_UNIT | O |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601. | M |
| Basic-Nu-Observed-Value | See ISO/IEEE 11073-20601—This indicates the insulin pump's wave amount in International Units (IU), ranging from 0.0 to 999.9 | M |

Pump Wave Duration
   Insulin pump's wave duration BCD Number (hhmm) 0x0000-0x9959

| Attribute Name | Value | Qualifier |
|---|---|---|
| Type | MDC_PART_OBJ \| MDC_CTXT_RPC_PUMP_WAVE_DURATION | M |
| Unit-Code | | O |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601. | M |
| Basic-Nu-Observed-Value | See ISO/IEEE 11073-20601—This indicates the insulin pump's wave duration in hours and minutes (BCD format). | M |

Appendix B

Common RPC Enumeration Object Attributes

| Attribute Name | Value | Qualifier |
|---|---|---|
| Handle | The Handle attribute represents a reference ID for this object. Each object shall have a unique ID assignment by the agent. | M |
| Type | Defined in each of the enumeration objects. | M |
| Metric-Spec-Small | mss-avail-intermittent \| mss-avail-stored-data \| mss-upd-aperiodic \| mssacc-agent-initiated \| mss-cat-manual. | M |

-continued

| Attribute Name | Value | Qualifier |
|---|---|---|
| Attribute-Value-Map | Defined in each of the enumeration objects. | M |
| Absolute-Time-Stamp | AbsoluteTime as defined in ISO/IEEE 11072-20601 | M |
| Enum-Observed-Value-Simple-OID | The value is reported as a nomenclature code. One and only one of Enum-Observed-Value-Simple-OID, Enum-Observed-Value-Basic-Bit-Str shall be present | C |
| Enum-Observed-Value-Basic-Bit-Str | The value is reported as a bit string of 32-bits. One and only one of Enum-Observed-Value-Simple-OID, Enum-Observed-Value-Basic-Bit-Str, Enum-Observed-Value-Simple-Str shall be present. | C |
| Enum-Observed-Value-Simple-Str | The value is reported as an ASCII printable string. One and only one of Enum-Observed-Value-Simple-OID, Enum-Observed-Value-Basic-Bit-Str, Enum-Observed-Value-Simple-Str shall be present | C |

Timeblock (Meal Segment)

| Attribute Name | Value | Qualifier |
|---|---|---|
| Type | MDC_PART_OBJ \| MDC_CTXT_RPC_MEAL_SEG_TIMEBLOCK | M |
| Attribute-Value-Map | MDC_ATTR_ENUM_OBS_VAL_SIMP_OID, then MDC_ATTR_TIME_STAMP_ABS | M |
| Absolute-Time-Stamp | AbsoluteTime as defined in ISO/IEEE 11073-20601. | M |
| Enum-Observed-Value-Simple-OID | Valid values are RPC_MEAL_SEG_TIME_NT RPC_MEAL_SEG_TIME_BB RPC_MEAL_SEG_TIME_AB RPC_MEAL_SEG_TIME_BL RPC_MEAL_SEG_TIME_AL RPC_MEAL_SEG_TIME_BD RPC_MEAL_SEG_TIME_AD RPC_MEAL_SEG_TIME_EV | M |

Structured Test Type

| Attribute Name | Value | Qualifier |
|---|---|---|
| Type | MDC_PART_OBJ \| MDC_CTXT_RPC_ST_TYPE | M |
| Attribute-Value-Map | MDC_ATTR_ENUM_OBS_VAL_SIMP_OID, then MDC_ATTR_TIME_STAMP_ABS | M |
| Absolute-Time-Stamp | AbsoluteTime as defined in ISO/IEEE 11073-20601. | M |
| Enum-Observed-Value-Simple-OID | Valid values are RPC_STRUCTURED_TEST_3_DAY_SNAP \| RPC_STRUCTURED_TEST_BIT | M |

Structured Test Time Event

| Attribute Name | Value | Qualifier |
|---|---|---|
| Type | MDC_PART_OBJ \| MDC_CTXT_RPC_MEAL_SEG_TIME_EVENT | M |
| Attribute-Value-Map | MDC_ATTR_ENUM_OBS_VAL_SIMP_OID, then MDC_ATTR_TIME_STAMP_ABS | M |
| Absolute-Time-Stamp | AbsoluteTime as defined in ISO/IEEE 11073-20601. | M |
| Enum-Observed-Value-Simple-OID | Valid values are RPC_ST_TIME_EVENT_BB RPC_ST_TIME_EVENT_AB RPC_ST_TIME_EVENT_BL RPC_ST_TIME_EVENT_AL RPC_ST_TIME_EVENT_BD RPC_ST_TIME_EVENT_AD RPC_ST_TIME_EVENT_BT | M |

Structured Test Protocol Events

| Attribute Name | Value | Qualifier |
| --- | --- | --- |
| Type | MDC_PART_OBJ \| MDC_CTXT_RPC_ST_PROTOCOL_EVENT | M |
| Attribute-Value-Map | MDC_ATTR_ENUM_OBS_VAL_SIMP_OID, then MDC_ATTR_TIME_STAMP_ABS | M |
| Absolute-Time-Stamp | AbsoluteTime as defined in ISO/IEEE 11073-20601. | M |
| Enum-Observed-Value-Simple-OID | Valid values are RPC_ST_MISSED_BG_ACQUISITION RPC_ST_MISSED_INSULIN_ADMINISTRATION RPC_ST_EXIT_NO_REASON RPC_ST_EXIT_TIME_LIMIT_EXCEEDED RPC_ST_EXIT_GOAL_REACHED RPC_ST_EXIT_TOO_MANY_SEVEREHYPOS RPC_ST_EXIT_TOO_MANY_HYPOS RPC_ST_EXIT_ADHERENCE RPC_ST_EXIT_PROTOCOL RPC_ST_EXIT_MAXIMUMDOSE RPC_ST_EXIT_INVALIDDATETIME RPC_ST_EXIT_INVALIDPARAM | M |

Structured Test Configuration Change

| Attribute Name | Value | Qualifier |
| --- | --- | --- |
| Type | MDC_PART_OBJ \| MDC_CTXT_RPC_ST_CONFIG_CHANGE | M |
| Unit-Code | | O |
| Attribute-Value-Map | MDC_ATTR_ENUM_OBS_VAL_SIMP_OID, then MDC_ATTR_TIME_STAMP_ABS | M |
| Absolute-Time-Stamp | AbsoluteTime as defined in ISO/IEEE 11073-20601. | M |
| Enum-Observed-Value-Simple-OID | See section 6.1.1.19 for Structured Test Parameter definitions | M |

What is claimed is:

1. A computer-implemented diabetes management system that employs a communication protocol with enhanced security, comprising:
   a medical device operable to perform a diabetes care function in relation to a patient and store data related to the operation thereof; and
   a diabetes care manager in data communication with the medical device using a communication protocol defined in accordance with IEEE standard 11073 and operable to request access to a given security role supported by the medical device, wherein the diabetes care manager authenticates with the medical device using a set of authentication commands and a public key assigned to the given security role, wherein the given security role is associated with a set of commands that are defined as a private extension of the communication protocol and the set of authentication commands are defined as a private extension of the communication protocol.

2. The diabetes management system of claim 1 wherein the diabetes care manager issues a request command from the set of commands to the medical device, and the medical devices receives the issued request command and issues a response command in response thereto when the diabetes care manager is authenticated by the medical device.

3. The diabetes management system of claim 1 wherein the medical device is configured with software and the diabetes care manager upgrades the software on the medical device using the set of commands.

4. The diabetes management system of claim 1 wherein the medical device executes a structured collection procedure to obtain measures of a physiological variable from a patient and the diabetes care manager accesses and manipulates parameters of the structured collection procedure using the set of commands.

5. The diabetes management system of claim 1 wherein the diabetes care manager issues a request command from another set of commands to the medical device without authenticating with the medical device, and the medical device receives the issued request command and issues a response command in response thereto.

6. The diabetes management system of claim 5 wherein the another set of commands are defined in the IEEE standard 11073.

7. The diabetes management system of claim 1 wherein the medical device supports a plurality of security roles, including a first security role associated with a first set of commands for accessing data and a second security role associated with a second set of commands for accessing data, the second set of commands having one or more commands that are mutually exclusive from the first set of commands.

8. A computer-implemented diabetes management system that employs a communication protocol with enhanced security, comprising:
   a medical device that supports a plurality of security roles for accessing the data residing thereon;
   a diabetes care manager in data communication with the medical device using a communication protocol defined in accordance with IEEE standard 11073;
   a first application residing on the diabetes care manager and operable to request access to a first security role supported by the medical device, wherein the first application having a first public key assigned to the first security role and the first security role is associated with a first set of commands for accessing data on the medical device;

a second application residing on the diabetes care manager and operable to request access to a second security role supported by the medical device, wherein the second application having a second public key distinct from the first public key and assigned to the second security role and the second security role is associated with a second set of commands for accessing data on the medical device, the second set of commands having one or more commands that are mutually exclusive from the first set of commands and the first set of commands and the second set of commands are defined as a private extension of the communication protocol; and wherein the diabetes care manager authenticates with the medical device using a set of authentication commands and the applicable public key, where the set of authentication commands are defined as a private extension of the communication protocol.

9. The diabetes management system of claim 8 wherein the diabetes care manager issues a request command from the set of commands to the medical device, and the medical devices receives the issued request command and issues a response command in response thereto when the diabetes care manager is authenticated by the medical device.

10. The diabetes management system of claim 8 wherein the medical device is configured with software and the first application upgrades the software on the medical device using the first set of commands.

11. The diabetes management system of claim 8 wherein the medical device executes a structured collection procedure to obtain measures of a physiological variable from a patient and the second application accesses and manipulates parameters of the structured collection procedure using the second set of commands.

12. The diabetes management system of claim 8 wherein the diabetes care manager issues a request command from another set of commands to the medical device without authenticating with the medical device, and the medical device receives the issued request command and issues a response command in response thereto.

13. The diabetes management system of claim 12 wherein the another set of commands are defined in the IEEE standard 11073.

14. A medical device system that employs a communication protocol with enhanced security, comprising:

a medical device that supports a plurality of security roles for accessing the data residing thereon;

a data manager in data communication with the medical device using a communication protocol defined in accordance with IEEE standard 11073;

a first application residing on the manager and operable to request access to a first security role supported by the medical device, wherein the first application having a first public key assigned to the first security role and the first security role is associated with a first set of commands for accessing data on the medical device;

a second application residing on the manager and operable to request access to a second security role supported by the medical device, wherein the second application having a second public key distinct from the first public key and assigned to the second security role and the second security role is associated with a second set of commands for accessing data on the medical device, the second set of commands having one or more commands that are mutually exclusive from the first set of commands and the first and second set of commands are defined as a private extension of the communication protocol; and wherein the data manager authenticates with the medical device using a set of authentication commands and the applicable public key, where the set of authentication commands are defined as a private extension of the communication protocol.

15. The medical device system of claim 14 wherein the data manager issues a request command from the set of commands to the medical device, and the medical devices receives the issued request command and issues a response command in response thereto when the data manager is authenticated by the medical device.

16. The medical device system of claim 14 wherein the medical device is configured with software and the first application upgrades the software on the medical device using the first set of commands.

17. The medical device system of claim 14 wherein the medical device executes a structured collection procedure to obtain measures of a physiological variable from a patient and the second application accesses and manipulates parameters of the structured collection procedure using the second set of commands.

* * * * *